United States Patent [19]

Saksena

[11] Patent Number: 4,944,300
[45] Date of Patent: Jul. 31, 1990

[54] METHOD FOR HIGH ENERGY DEFIBRILLATION OF VENTRICULAR FIBRILLATION IN HUMANS WITHOUT A THORACOTOMY

[76] Inventor: Sanjeev Saksena, 33 Fairway Dr., Glenbrook, N.J. 08812

[21] Appl. No.: 463,843

[22] Filed: Jan. 12, 1990

Related U.S. Application Data

[63] Continuation of Ser. No. 43,489, Apr. 28, 1987, abandoned.

[51] Int. Cl.$^5$ .............................................. A61N 1/00
[52] U.S. Cl. .............................................. 128/419 D
[58] Field of Search ............... 128/419 D, 419 P, 784, 128/785

[56] References Cited

U.S. PATENT DOCUMENTS

| | | | |
|---|---|---|---|
| 3,706,313 | 12/1972 | Milani et al. | 128/419 D |
| 4,030,509 | 6/1977 | Heilman et al. | 128/419 D |
| 4,270,549 | 6/1981 | Heilman | 128/419 D |
| 4,548,203 | 10/1985 | Tacker, Jr. et al. | 128/419 D |
| 4,559,946 | 12/1985 | Mower | 128/419 D |
| 4,662,377 | 5/1987 | Heilman et al. | 128/419 P |
| 4,708,145 | 11/1987 | Tacker, Jr. et al. | 128/419 D |

OTHER PUBLICATIONS

Saksena, S., Calvo, R. A., Pantopoulos, D., Gordon, S., Gadhoke, A., "Simultaneous Shocks for Ventricular Tachycardia Cardioversion: Effect of Electrode Position on Efficacy", presented at the May 1986 meeting in Washington, D.C. of the American Federation of Clinical Research; Clin Res 34:341A, 1986.
Saksena, S., Calvo, R. A., Pantopoulos, D., Rothbart, S. T., Gadhoke, A., "Cardioversion of Rapid Ventricular Tachycardia with Two Simultaneous Transvenous Shocks in Man", presented at the May 1986 meeting in Washington, D.C. of the American Federation of Clinical Research; Clin Res 34:341A, 1986.
Saksena, S., Chandran, P., Shah, Y., Boccadomo, R., Pantapoulos, D., "Comparative Efficacy of Transvenous Cardioversion and Pacing in Sustained Ventricular Tachycardia-A Prospective, Randomized Crossover Study", Cir 72:153-160, 185.
Saksena, S., Calvo, R., "Transvenous Cardioversion for Ventricular Tachyarrhythmias: Current Status and Future Directions", PACE 8:715-731, 1985.
Jones, D. L., Klein, G. J., Guiraudon, G. M., Sharma, A. D., Kallok, M. J., Bourland, J. D., and Tacker, W. A., "Internal Cardiac Defibrillation in Man: Pronounced Improvement with Sequential Pulse Delivery to Two Different Head Orientations," Circ 73:484-491, Mar. 1986.
Saksena, S., Ciccone, J., Rothbart, S. T., Liptak, K., Craelius W., "Efficacy of Transvenous Cardioversion in Ventricular Tachycardia: A Prospective Randomized Study", J Am Coll Cardio 3:554, 1984.
Shah, Y., Saksena, S., Ciccone, J., Rothbart, S. T., Tranotti, K., Pantopoulos, D., "Factors Influencing the Efficacy of Transvenous Cardioversion for Sustained Ventricular Tachycardia", Clin Res 32:205A, 1984.
Saksena, S., Ciccone, J., Rothbart, S. T., Liptak, K., Craelius, W., "A Prospective Randomized Study of Transvenous Cardioversion in Ventricular Tachycardia", Eur Ht J 5: Suppl I, p. 229, 1984.
Saksena, S., Pantopoulos, D., Parsonnet, V., Rothbart, S. T., Hussain, S. M., Gielchinsky, I., Lombardo, S., "The Value of an Implantable Antitachycardia System in Patients with Recurrent Sustained Tachycardias", Clin Res 32:203A, 1984.
Saksena, S., Shah, Y., Boccodamo, R., Rothbart, S. T., "Comparative Efficacy of Transvenous Cardioversion and Pacing in Ventricular Tachycardia: A Prospective Randomized Crossover Study", Circ 70 (Suppl II): II-406, 1984.
Calvo, R., Saksena, S., Rothbart, S. T., Pantopoulos, D., "Efficacy and Safety of a Combined Pacing and Transvenous Cardioversion Algorithm in Ventricular Tachycardia: A Prospective Randomized Study", Cir 72 (Suppl III): III-383, 1985.
Rothbart, S. T., Saksena, S., Pantopoulos, D., Calvo, R., "Efficacy and Safety of Transvenous Cardioversion of Rapid Ventricular Tachycardia Using Two Energy Waveforms: A Prospective Randomized Study", J AM Coll Cardiol 7:73A, 1986.
Saksena, S., Rothbart, S. T., Calvo, R., Pantopoulos, D., Hussain, S. M., "Mechanism of Efficacy of Transvenous Cardioversion of Ventricular Tachyarrhythmias as Determined by Cardiac Mapping in Man", J Am Coll Cardiol 7:73A, 1986.
Saksena, S., Calvo, R. A., Pantopoulos, D., Rothbart, S. T., Gadhoke, A., "Cardioversion of Rapid Ventricular Tachycardia with Two Simultaneous Transvenous Shocks in Man", presented at the May 1986 meeting in Washington, D.C. of the American Federation of Clinical Research; Clin Res 34:341A, 1986.
Saksena, S., Calvo, R. A., Pantopoulos, D., Gordon, A., Gadhoke, A., "Simultaneous Shocks for Ventricular Tachycardia Cardioversion: Effect of Electrode Position", Proc X World Congr of Cardiol, p. 483, Sep. 1986.
Calvo, R., Saksena, S., Rothbart, S. T., Pantopoulos, D., Gadhoke, A., "Comparison of a Single and Two Simultaneous Transvenous Shocks in Rapid Ventricular Tachycardia", Proc X World Congr of Cardiol, p. 1985, Sep. 1986.

(List continued on next page.)

Primary Examiner—Francis Jaworski
Assistant Examiner—George Manuel
Attorney, Agent, or Firm—Kenyon & Kenyon

[57] ABSTRACT

Defibrillation of ventricular fibrillation and cardioversion of ventricular tachycardia is accomplished by single, bidirectional high energy shocks from two anodes to a common cathode. All the electrical apparatus is implanted without a thoracotomy.

4 Claims, No Drawings

OTHER PUBLICATIONS

Mehra, R., and Marcaccini, S., "Comparison of Sequential Pulse Debibrillation Threshold with a Non-Epicardial Electrode System", Circ 74:II-184, Oct. 1986.

Lindsay, E. D., Rothbart, S. T., Wasty, N., Pantopoulos, D., Saksena, S., "Prospective Evaluation of Ventricular Pacing and High Energy Transvenous Shocks Using a Triple Electrode Array for Cardioversion of Ventricular Tachycardia", J Am Coll Cardiol 9:141A, Feb., 1987.

Saksena, S., Rothbart, S. T., Lindsay, B. D., Calvo, R. A., Pantopoulos, D., "Is There an Optimal Termination Algorithm for the Transvenous Cardioversion of Ventricular Tachycardia?", PACE, vol. 10, p. 416, Mar.-Apr. 1987.

Saksena, S., Rothbart, S. T., Calvo, R. A., Pantopoulos, D., "Comparison of Single and Dual Current Pathways for Transvenous Cardioversion in Rapid Ventricular Tachycardia", PACE 10:446, Mar.-Apr. 1987.

METHOD FOR HIGH ENERGY DEFIBRILLATION OF VENTRICULAR FIBRILLATION IN HUMANS WITHOUT A THORACOTOMY

This application is a continuation of application Ser. No. 043,489, filed Apr. 28, 1987, now abandoned.

This invention relates to a method for defibrillating ventricular fibrillation and cardioversion of ventricular tachycardia in humans by means of single bidirectional high energy electrical shocks from implanted shock generator apparatus.

Ventricular fibrillation is an irregular uncoordinated action of the fibers of the heart muscle, which results in a failure of the heart to pump blood. Unless corrective action is taken promptly, death results in a few minutes.

Ventricular tachycardia also involves some irregularity of the rythmic action of the heart muscle but is primarily characterized by an abnormally fast and altered contraction pattern. Ventricular tachycardia is subject to being accelerated into ventricular fibrillation by a number of known factors or stimuli, including inadvertently by means of electrical impulses from a cardioverter apparatus.

These disorders (ventricular fibrillation and ventricular tachycardia) result in cessation of adequate pump function of the heart and sudden cardiac death. This is the leading cause of death in the United States; it is believed that more than 300,000 individuals in the United States experience such events annually.

Implantable pacemakers have been employed for several years. They are characterized by employing electrical impulses of relatively low energy. They are useful for a few selected patients having ventricular tachycardia with rates below 200 beats per minute, but not for a much larger number of patients who chronically or on occasion have faster ventricular tachycardia. Pacemakers are ineffective for defibrillating ventricular fibrillation, and are known to have inadvertently accelerated ventricular tachycardia into ventricular fibrillation on some occasions.

Cardioverter and/or defibrillator devices have been in development for more than a decade. Early prototypes employed a pair of electrodes disposed on a catheter inserted into the heart transvenously. One electrode, serving as a cathode, was located at the distal end of the catheter and positioned in the right ventricle near the apex thereof. A second electrode on the catheter was positioned in the right atrium of the heart or at the superior vena cava. Cardioversion or defibrillation was accomplished by shocks of electrical energy, passing from the anode to the cathode, lasting a few to several milliseconds. The foregoing procedure is characterized as a uni-directional electrical shock.

U.S. Pat. No. 4,548,203 describes a process of sequential bidirectional shocks, in which two separate shocks are released, from two spatially separated anodes in a timed sequence. As depicted in FIG. 3a, a cathode and a first anode electrode, both catheter-borne, are positioned, respectively, in the right ventricle and the superior vena cava, as described above. A second anode electrode is positioned on the outside of the left ventricle. In operation according to the method described in such patent, a first electrical shock is passed between one anode and the cathode, and shortly thereafter, a second shock is passed from the second anode to the cathode. Thus, the foregoing is referred to as a sequential, bidirectional system. In an alternative configuration described in the patent, two pairs of electrodes may be employed, as depicted in FIG. 2. Each electrode of a pair is positioned opposite the other and in the pericardial space between the outer surface of the heart (the epicardium) and the sac (the pericardium) enclosing the heart. The four electrodes are orthogonal to each other. In this configuration, there is no catheter-borne electrode. In operation, a first shock is passed between two electrodes forming one pair, and the shortly thereafter, a second shock is passed between the electrodes of the second pair.

The foregoing sequential, bidirectional method of imparting electrical shocks to the heart has two distinct disadvantages. One is that a thoracotomy (i.e., an opening of the chest wall) is required. This fact is apparent from FIGS. 10-12, depicting a part of the surgical procedure for positioning pairs of electrodes in the pericardial space, and also from the location, on the outer left ventricle, of the second anode 37 of FIG. 3a.

Secondly, an inherent requirement of a sequential shock system is the necessity of having two capacitors and two power sources as part of the shock-generating apparatus. This necessity is a significant disadvantage in respect of implantable apparatus, because it inherently increases the size and weight of the apparatus relative to that which can be designed specifically for a single shock, bidirectional system as described hereinafter.

As of the current time, the method described in U.S. Pat. No. 4,548,203 has never been employed as a human implant system for defibrillation of ventricular fibrillation or cardioversion of ventricular tachycardia.

The sequential, bidirectional system with electrodes positioned as in FIG. 3a of U.S. Pat. No. 4,548,203 is also described by D. L. Jones, et al., in "Internal Cardiac Defibrillation In Man: Pronounced Improvement With Sequential Pulse Delivery To Two Different Lead Orientations", *Circulation*, vol. 73, No. 3, pages 484–491 (March 1986). Such article describes the application of the method to human patients, including the fact that the chest wall was opened by means of a mediam sternotomy. There is no reference in the article to actually implanting the shock generator apparatus and electrodes.

It is accordingly an object of this invention to provide a method for the defibrillation of ventricular fibrillation or the cardioversion of ventricular tachycardia by means of single, bidirectional, high energy electrical shocks administered to the heart by means of implanted electrodes and implanted shock generator apparatus.

The method is for the high energy defibrillation of ventricular fibrillation or ventribular tachycardia in humans. It comprises subjecting the heart to a single, bidirectional high energy electrical shock from a first anode and a second anode to a cathode. The energy of the shock is at least 15 Joules, delivered over a period of time of not less than about 2 milliseconds to the anodes by an implanted shock generator. The cathode is transvenously positioned in the right ventricle. The first anode is transvenously positioned near the superior vena cava or in the right atrium. The second anode is positioned subcutaneously in the left half side of the chest and outside the rib cage. The two anodes are electrically connected in parallel to the shock generator. Both anodes and the cathode are electrically connected to the shock generator via implanted leads. The three electrodes, the leads and the shock generator are implanted without a thoracotomy.

For the defibrillation of ventricular fibrillation or cardioversion of ventricular tachycardia, the wave form of the electrical shock may be truncated exponential, rectangular, biphasic or sinusoidal. A truncated exponential wave form is preferred, having a tilt in the range of from about 15 degrees to about 80 degrees. The initial voltage at the start of the shock should be not less than about 300 volts, and may be as high as 600–750 volts. The trailing edge of a truncated wave form should be not less than 50 volts. The duration of the shock should be at least about 2 milliseconds, and may be much longer, such as 30–60 milliseconds, although usually a maximum of 15 milliseconds will suffice. The amount of energy employed per shock should be at least 15 Joules, and preferably from about 25 to about 30 Joules, for defibrillation or cardioversion of ventricular tachycardia. Additional energy may be employed providing the amount is not so great as to damage the tissue of the heart.

The defibrillation method may also optionally comprise imparting a second shock, in the same manner as the first shock, within about two minutes of the termination of the latter. The shock generator apparatus may also be designed to impart a third or a fourth shock.

It will be understood by those skilled in defibrillation of ventricle fibrillation and cardioversion of ventricular tachycardia that the minimum effective, and the maximum permissible, shock energy, voltage and duration for defibrillation varies from human to human, depending upon many factors, including illustratively the size and condition of an individual heart. This lack of uniformity, which is typical of medical science, precludes a precise quantitative statement of the ranges of physical parameters which will be uniformly applicable to all humans under all conditions.

Apparatus with which to practice the invention has been developed previously. The apparatus includes a catheter adapted to be transvenously inserted into the heart, and bearing at its distal end an electrode adapted to serve as a cathode, and, about 10–15 centimeters towards the proximal end, an electrode adapted to serve as a first cathode. The second anode is typically a patch electrode positioned subcutaneously outside the rib cage in the left half of the upper torso and above the diaphragm (i.e. outside the left anterior and posterior of the chest wall). The second anode is preferably positioned under any muscle which exists at the location selected. It is also preferably located in a horizontal plane through the fourth left intercostal (rib) space at the mid-axillary (arm pit) line.

The shock-generating apparatus should be implantable and deliver a single shock discharge. Thus such apparatus can be designed with only a single discharge capacitor if desired. The shock-generating apparatus is connected through implanted leads to the electrodes described herein. The first and second anodes are connected in parallel electrically to a discharge capacitor of the shock generator apparatus. Optionally, such apparatus may also have sensing means for sensing and measuring the action of the heart and initiating an electrical shock of pre-programmed duration and amount of energy in response to such sensing means. Although currently known shock-generator apparatus may be employed, it is anticipated that refinements in the design thereof for use in the single shock, bidirectional process described herein can result in apparatus of lesser size and weight and therefore be more acceptable to patients and surgeons.

The drawing depicts apparatus that may be employed in practicing the process described and claimed herein. The drawing shows the upper portion, from the neck to the midsection, of a human torso 10, having a heart 12. A catheter 14 is shown transvenously inserted into heart 10. The catheter bears at its distal end an electrode adapted to serve as a cathode 16, and positioned in the right ventricle of the heart 12. A first anode 18 is borne by the catheter 14 at a point about 10–15 centimeters from the distal end thereof, and positioned near the superior vena cava or in the right atrium of the heart 12. A second anode 20, such as a patch electrode, is disposed subcutaneously outside the torso's rib cage. It is preferably located along the mid-axillary (arm pit) line in a horizontal plane through the fourth left intercostal (rib) space, but for the sake of ease of understanding and clarity of depiction in the drawing, said second anode 20 is shown displaced somewhat to the right of said mid-axillary line.

First anode 18 and second anode 20 are connected electrically in parallel via implanted leads 22 and 24 to the discharge terminal of a capacitor (not shown) in an implanted shock generator apparatus 26, illustratively of the type referred to in the following paragraph. The sets 28 and 30 of dashed lines depict the pathway of electrical energy from, respectively, the first anode 18 and the second electrode 20, to the cathode 16.

The method described herein has been recently employed in a man aged 69 employing an implanted permanent non-epicardial triple electrode system in a patient with recurrent ventricular tachycardia and ventricular fibrillation and severe pulmonary disease who could not undergo an operation involving open chest surgery. A large patch electrode was placed over the rib cage in the mid-axillary line at the level of the left fourth intercostal space. A tripolar catheter was placed in the right ventricular apex and was used for sensing and shock delivery. An intracardiac cardioversion-defibrillation catheter (ICDC), available from Cardiac Pacemakers, Inc., of Minneapolis, Minn., was employed. The distal right ventricular electrode was the common cathode. The proximal superior vena cava/right atrial electrode and the subcutaneous patch were cross-connected with a Y-connector as dual anodes. Employing the foregoing configuration and apparatus, a single 10 Joule bidirectional shock resulted in successful defibrillation of ventricular fibrillation during testing with an external shock generator prior to implanting a permanent shock generator. The defibrillation threshold was less than 10 Joules. The implanted shock generator was an Automatic Implantable Cardioverter/Defibrillator, also available from Cardiac Pacemakers, Inc. Postoperative electrophysiologic studies demonstrated continued successful defibrillation of ventricular fibrillation with the foregoing system.

Having thus described the invention, what is claimed is:

1. A method for the high energy defibrillation of ventricular fibrillation or cardioversion of ventricular tachycardia in humans, which comprises subjecting the heart to a single bidirectional high energy electrical shock from a first anode and a second anode to a cathode, said shock comprising at least 15 Joules over a period of time of not less than about 2 milliseconds and being delivered to said anodes by an implanted shock generator, said cathode being transvenously positioned in the right ventricle, said first anode being transvenously positioned near the superior vena cava or in the right atrium, said second anode being positioned subcutaneously in the left half side of the chest and outside the rib cage near the axillary line and about at the level of the left fourth intercostal space, said anodes being electrically connected in parallel to said shock generator, said anodes and cathode being connected to said shock generator via implanted leads, and said anodes, cathode, leads and shock generator apparatus having been put into position without a thoracotomy.

2. The method of claim 1 wherein the minimum initial voltage of said shock is at least 300 volts.

3. The method of claim 2 wherein said shock has a truncated exponential wave form and a tilt in the range of from about 15 degrees to about 80 degrees, and the trailing voltage at the end of the shock is not less than about 50 volts.

4. The method of claim 1 in which a second electrical shock is discharged within about two minutes of said first shock.

* * * * *

UNITED STATES PATENT AND TRADEMARK OFFICE
CERTIFICATE OF CORRECTION

PATENT NO. : 4,944,300
DATED : July 31, 1990
INVENTOR(S) : Sanjeev Saksena It is certified that error appears in the above-identified patent and that said Letters Patent is hereby corrected as shown below:

Col. 2, line 10, delete "the".

Col. 2, lines 41-42, change "mediam" to --median--.

Col. 2, line 52, change "ventribular" to --ventricular--.

In the inventor's address change "Glenbrook" to --Green Brook--.

Col. 3, line 26, change "ventricle" to --ventricular--.

In Item [56] Reference Cited:, under Other Publications, page 2, change "Debibrillation" to --Defibrillation--.

Signed and Sealed this

Fourteenth Day of January, 1992

Attest:

HARRY F. MANBECK, JR.

Attesting Officer

Commissioner of Patents and Trademarks